(12) United States Patent
Muyari (10) Patent No.: US 8,262,654 B2
(45) Date of Patent: Sep. 11, 2012

(54) HIGH-FREQUENCY TREATMENT INSTRUMENT

(75) Inventor: Yuta Muyari, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1141 days.

(21) Appl. No.: 11/809,080

(22) Filed: May 31, 2007

(65) Prior Publication Data

US 2007/0282327 A1 Dec. 6, 2007

(30) Foreign Application Priority Data

Jun. 1, 2006 (JP) ................. P2006-153151

(51) Int. Cl.
*A61B 18/14* (2006.01)
(52) U.S. Cl. .................................. 606/47; 606/46
(58) Field of Classification Search ............ 606/41, 606/45–52
See application file for complete search history.

(56) References Cited

U.S. PATENT DOCUMENTS

| | | | | |
|---|---|---|---|---|
| 5,064,424 A | * | 11/1991 | Bitrolf | 606/46 |
| 5,192,280 A | * | 3/1993 | Parins | 606/48 |
| 5,456,684 A | * | 10/1995 | Schmidt et al. | 606/41 |
| 5,876,416 A | | 3/1999 | Hill | |
| 6,663,626 B2 | * | 12/2003 | Truckai et al. | 606/41 |
| 7,549,991 B2 | * | 6/2009 | Lu et al. | 606/50 |
| 2002/0019632 A1 | | 2/2002 | Mayenberger | |
| 2004/0172081 A1 | | 9/2004 | Wang | |
| 2004/0254571 A1 | * | 12/2004 | Iki et al. | 606/41 |
| 2005/0101945 A1 | | 5/2005 | Sakurai et al. | |

FOREIGN PATENT DOCUMENTS

| | | |
|---|---|---|
| EP | 0 624 348 A2 | 11/1994 |
| JP | 08-299355 | 11/1996 |
| JP | 2003-299667 | 10/2003 |
| JP | 2004-261372 | 9/2004 |
| JP | 2005-110861 | 4/2005 |
| JP | 2005-270241 | 10/2005 |

* cited by examiner

*Primary Examiner* — Michael Peffley
(74) *Attorney, Agent, or Firm* — Scully, Scott, Murphy & Presser, P.C.

(57) ABSTRACT

The high-frequency treatment instrument is a high-frequency treatment instrument for performing a high-frequency treatment on a pathological lesion portion (subject tissue) not shown and includes a sheath (elongated extension member), a treatment electrode which is rotatably disposed at a distal end of the sheath and which extends in a direction substantially parallel to a diameter direction of the rotation, an operating wire (axial member) for allowing the treatment electrode to rotate around the distal end of the sheath, and an operating portion to which proximal ends of the sheath and the operating wire are connected. According to a high-frequency treatment instrument, by enabling a treatment on a subject tissue without using a curving operation of an endoscope it is possible to facilitate a procedure.

5 Claims, 13 Drawing Sheets

HIGH-FREQUENCY TREATMENT INSTRUMENT

BACKGROUND OF THE INVENTION

1. Field of the Invention

The present invention relates to a high-frequency treatment instrument.

Priority is claimed on Japanese Patent Application No. 2006-153, filed on Jun. 1, 2006, the content of which is incorporated herein by reference.

2. Description of the Related Art

As a treatment method of removing a biological tissue such as a mucous membrane by the use of an endoscope, an endoscopic submucosal dissection (ESD) method of cutting out a normal mucous membrane around a pathological lesion portion and then dissecting a submucosal layer to remove or the like the pathological lesion portion so as to remove the pathological lesion portion generated on a surface of an alimentary canal is known.

Various treatment instruments are used for such kind of dissecting treatment. For example, a high-frequency treatment instrument having a knife portion as a treatment electrode at a distal end of a rod-shaped electrode portion housed in a sheath is known (for example, see Japanese Unexamined Patent Application, First Publication No. H08-299355).

By the use of the high-frequency treatment instrument described in Japanese Unexamined Patent Application, First Publication No. H08-299355, it is possible to dissect the submucosal layer by allowing high-frequency current to flow in the knife portion to cut out a mucous membrane contacting the knife portion.

SUMMARY OF THE INVENTION

In a first aspect of the present invention, there is provided a high-frequency treatment instrument for performing a high-frequency treatment on a subject tissue, the high-frequency treatment instrument includes: an elongated extension member; and a treatment electrode that is rotatably connected to a distal end of the elongated extension member and that has a knife portion extending substantially parallel to a diameter direction of the rotation.

In a second aspect of the high-frequency treatment instrument of the present invention, the high-frequency treatment instrument includes the treatment electrode in which a pair of electrode pieces that rotate reversely to each other around the same rotation center is provided. In this case, each of the pair of electrode pieces has the knife portion.

In a third aspect of the high-frequency treatment instrument of the present invention, the high-frequency treatment instrument includes the elongated extension member of a tube shape. The high-frequency treatment instrument further includes an axial member that is rotatably connected to the treatment electrode and that advances and retreats relative to the elongated extension member to rotate the treatment electrode.

In fourth aspect of the high-frequency treatment instrument of the present invention, the high-frequency treatment instrument includes the knife portion which rotates from a state where the knife portion is substantially parallel to a center line direction of the elongated extension member to a state where the knife portion is substantially perpendicular to the center line direction.

In a fifth aspect of the high-frequency treatment instrument of the present invention, the high-frequency treatment instrument includes the knife portion in which a length thereof is greater than the outer diameter of the elongated extension member.

In a sixth aspect of the high-frequency treatment instrument of the present invention, there is provided a high-frequency treatment instrument for performing a high-frequency treatment on a subject tissue, the high-frequency treatment instrument includes: a sheath; an axial member disposed in the sheath so as to freely advance and retreat and to freely rotate; and a treatment electrode that is disposed at a distal end of the axial member so as to advance and retreat in the sheath along with the axial member and that has a knife portion extending in a direction substantially perpendicular to a center line of the axial member as the axial member being a center.

DETAILED DESCRIPTION OF THE INVENTION

A first embodiment of the invention will be described with reference to FIGS. 1 to 7.

Figure 1:
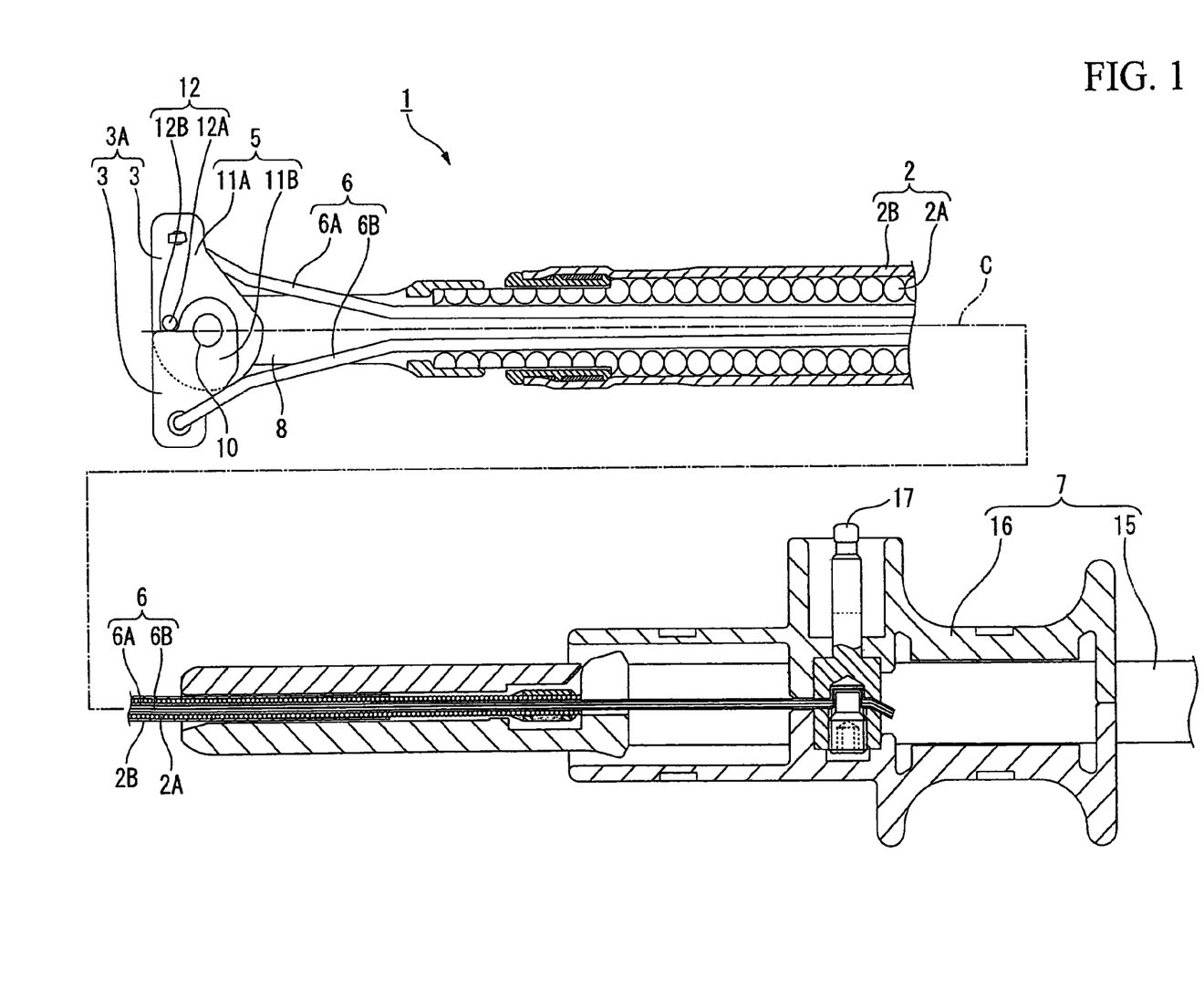
FIG. 1 is a partially sectional schematic view illustrating a whole high-frequency treatment instrument according to a first embodiment of the invention.
Figure 2A:
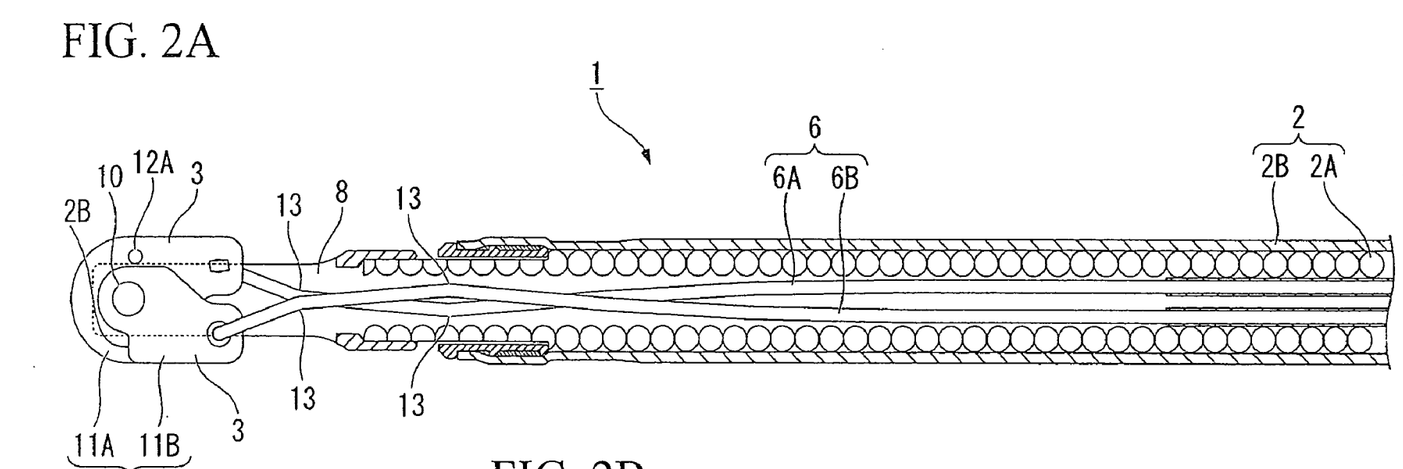
FIG. 2A is a partially sectional plan view of substantial part illustrating the high-frequency treatment instrument according to the first embodiment of the invention.
Figure 2B:
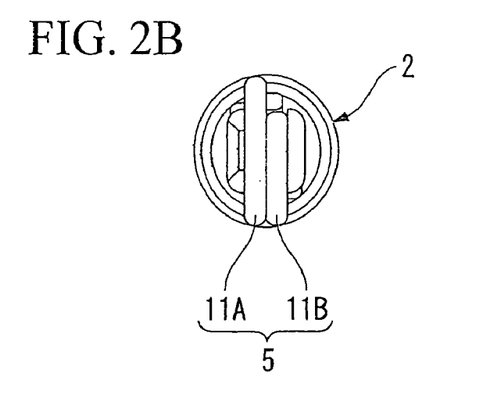
FIG. 2B is a partially-sectional front view of substantial part illustrating the high-frequency treatment instrument according to the first embodiment of the invention.
Figure 3:
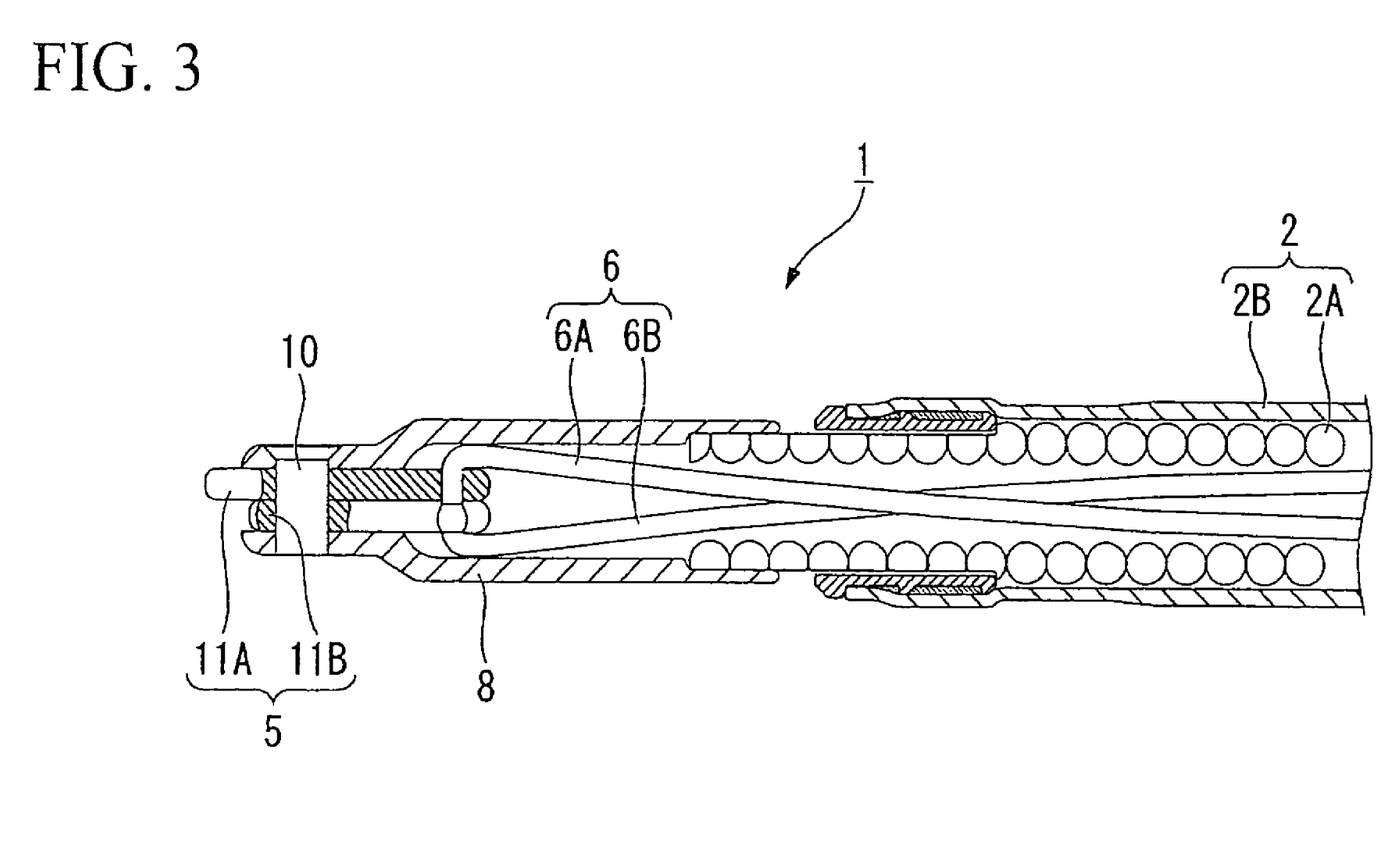
FIG. 3 is a partially-sectional side view of substantial part illustrating the high-frequency treatment instrument according to the first embodiment of the invention.

A high-frequency treatment instrument 1 according to the first embodiment of the invention is a high-frequency treatment instrument for performing a high-frequency treatment on a pathological lesion portion (subject tissue) not shown and includes a sheath (elongated extension member) 2, a treatment electrode 5 that is rotatably disposed at a distal end of the sheath 2 and that has a knife portion 3 extending in a direction substantially parallel to a diameter direction of the rotation, an operating wire (axial member) 6 for allowing the treatment electrode 5 to rotate around the distal end of the sheath 2, and an operating section 7 to which proximal ends of the sheath 2 and the operating wire 6 are connected, as shown in FIGS. 1 to 3.

The sheath 2 includes a coil sheath 2A in which a coil is wound to form a tube shape and a resin tube 2B which covers the coil sheath 2A. On the distal end of the sheath 2, a distal end support portion 8 which is disposed to protrude along a center line C of the sheath 2 and which rotatably supports the treatment electrode 5, is connected.

The treatment electrode 5 includes a pair of electrode pieces 11A and 11B that are connected to a distal end support 8 via an axis of rotation 10 and that rotate reversely to each other using the axis of rotation 10 as the same rotation center. Linear knife portions 3 are formed in the electrode pieces 11A and 11B, respectively. The knife portions 3 have a length substantially equal to the outer diameter of the sheath 2. When the knife portions 3 are made to rotate around the axis of rotation 10 from a state where the knife portions 3 are substantially parallel to the center line C of the sheath 2 to a state where the knife portions 3 are substantially perpendicular to the center line, the knife portions 3 are arranged linearly to form a cut-out surface 3A having a length substantially twice as long as the outer diameter of the sheath 2.

The length of the cut-out surface 3A is not limited to twice the outer diameter of the sheath 2, but may be any length which is longer than the outer diameter of the sheath 2.

A pair of electrode pieces 11A and 11B is provided with a stopper 12 for stopping the relative rotation thereof at the time of forming the cut-out surface 3A. The stopper 12 includes a convex portion 12A formed in the electrode piece 11A and a notch portion 12B formed in the electrode piece 11B on which the convex portion 12A is locked.

The operating wire 6 is disposed in the sheath 6 so as to freely advance and retreat. The distal end side of the operating wire 6 is branched into a first wire 6A rotatably connected to the electrode piece 11A and a second wire 6B rotatably connected to the electrode piece 11B. The first wire 6A and the second wire 6B are provided with a plurality of bent portions 13 which intersect each other in the sheath 2.

The operating section 7 includes an operating portion body 15 connected to a proximal end of the resin tube 2B and a slider 16 connected by a proximal end of the sheath 2 so as to freely slide relative to the operating portion body 15. An electrode terminal 17 electrically connected to the operating wire 6 and connected to a connection cable extending from a high-frequency power source not shown is disposed in the slider 16.

Next, operations of the high-frequency treatment instrument 1 will be described with reference to a procedure of removing a pathological lesion portion X generated on the surface of an alimentary canal by dissecting a submucosal layer W by the use of the high-frequency treatment instrument 1 according to this embodiment.

Figure 4:
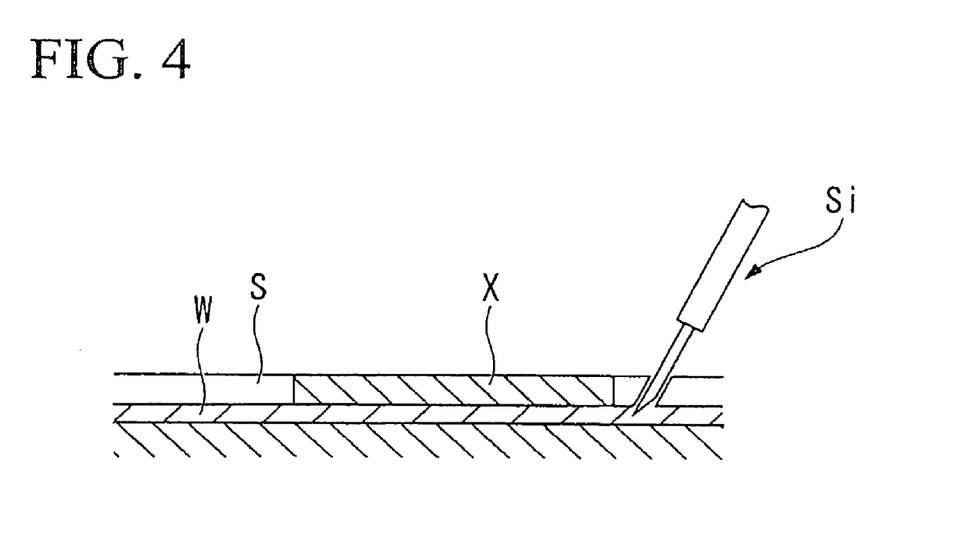
FIG. 4 is an explanatory diagram illustrating a usage example of the high-frequency treatment instrument according to the first embodiment of the invention.
Figure 5:
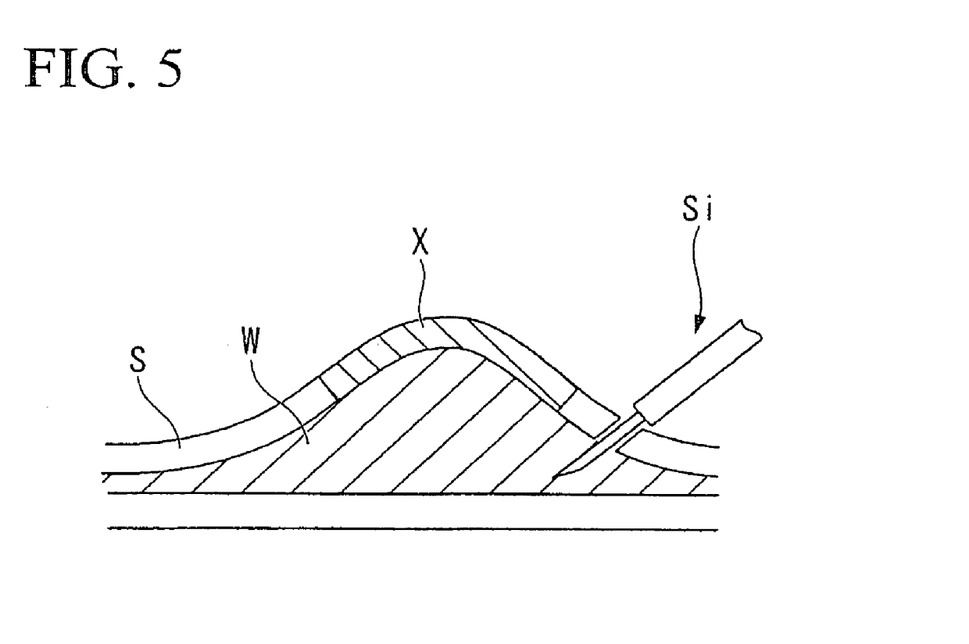
FIG. 5 is an explanatory diagram illustrating a usage example of the high-frequency treatment instrument according to the first embodiment of the invention.

First, as shown in FIG. 4, an injection needle Si is introduced into a body cavity through a treatment instrument channel of an endoscope not shown and a physiologic saline solution is locally injected into the submucosal layer W around the pathological lesion portion X to be removed, thereby distending the pathological lesion portion X as shown in FIG. 5. Before performing the local injection, it is preferable that a dye be applied around the pathological lesion portion X to clarify the boundary of the pathological lesion portion X, and then a mucous membrane S is marked at a plurality of positions surrounding the circumference of the pathological lesion portion X by the use of an existing high-frequency knife HK.

Figure 6:
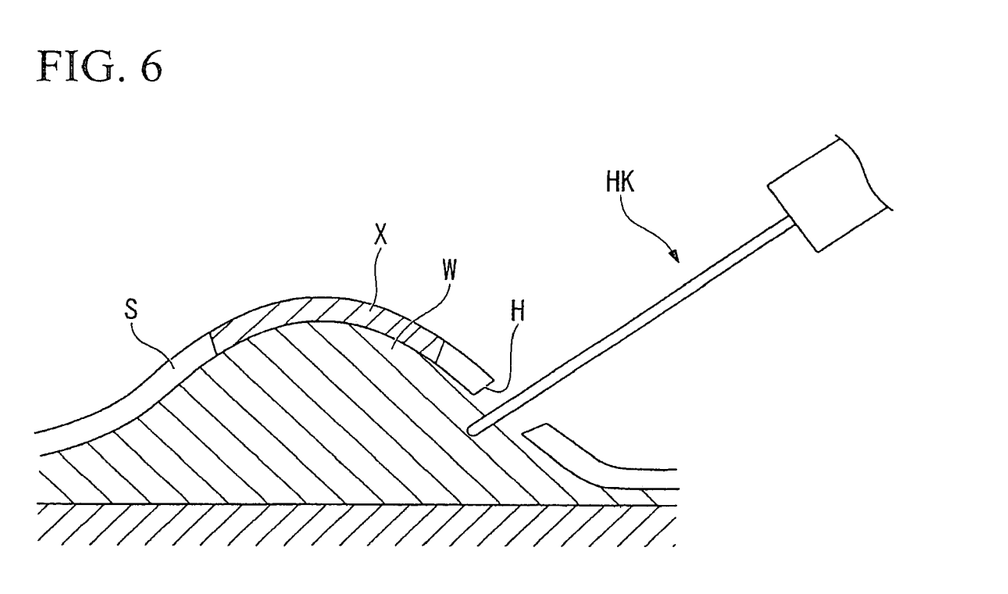
FIG. 6 is an explanatory diagram illustrating a usage example of the high-frequency treatment instrument according to the first embodiment of the invention.

Next, the existing high-frequency knife HK is inserted through the treatment instrument channel and is brought into contact with a part of the mucous membrane S in the vicinity of the pathological lesion portion X as shown in FIG. 6, and a hole H which is a start point of the entire peripheral cut-out is formed by supplying high-frequency current thereto. By operating both the endoscope and the high-frequency knife HK, the mucous membrane around the pathological lesion portion X is cut out to expose the submucosal layer W.

Then, the high-frequency knife is pulled out of the cannel and the sheath 2 of the high-frequency treatment instrument 1 is inserted into the channel. At this time, the slider 16 of the high-frequency treatment instrument 1 is made to retreat relative to the operating portion body 15, whereby the knife portions 3 of the pair of electrode pieces 11A and 11B are set to be substantially parallel to the center line C of the sheath 2 as shown in FIG. 2.

The treatment electrode 5 is exposed from the channel and then the slider 16 is made to move toward the distal end of the operating portion body 15. At this time, since the operating wire 6 advances relative to the sheath 2, the first wire 6A presses the electrode piece 11A and the second wire 6B presses the electrode piece 11B. Then, the electrode piece 11A rotates around the axis of rotation 10 in the counterclockwise direction in the drawing and the electrode piece 11B rotates in the clockwise direction. In this way, the linear cut-out surface 3A in a direction substantially perpendicular to the center line C of the sheath 2 is formed.

Figure 7:
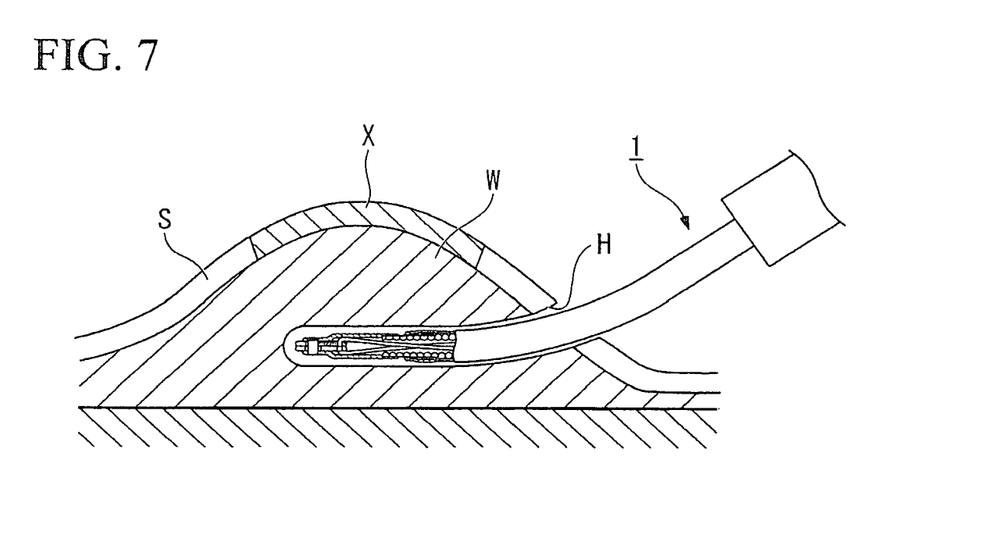
FIG. 7 is an explanatory diagram illustrating a usage example of the high-frequency treatment instrument according to the first embodiment of the invention.

High-frequency current is made to flow while the cut-out surface 3A is brought into contact with the submucosal layer W, and the sheath 2 of the high-frequency treatment instrument 1 is made to advance relative to the channel while observing with the endoscope. When the cut-out angle is to be changed, the operating portion 7 is made to rotate relative to the resin tube 2B. At this time, a rotation torque is transmitted to the treatment electrode 5 via the coil sheath 2A and the operating wire 6 and thus the treatment electrode rotates around the center line C, thereby changing the direction of the cut-out surface 3A. In this way, as shown in FIG. 7, the submucosal layer W is cut out and the pathological lesion portion X is dissected by the cut-out surface 3A.

According to the high-frequency treatment instrument 1, it is possible to adjust the contact angle between the cut-out surface 3A of the knife portions 3 and the pathological lesion portion X by rotating the treatment electrode 5 around the axis of rotation 10 and to bring the cut-out surface 3A of the knife portions 3 into contact with the pathological lesion portion X with an appropriate contact area by allowing the sheath 2 to advance and retreat relative to the endoscope. Accordingly, it is possible to enable a treatment on the pathological lesion portion X without performing a curving operation of the endoscope, thereby facilitating the procedure.

In the state where the knife portions 3 are substantially parallel to the center line C of the sheath 2, even when the knife portions 3 are elongated, the length of the treatment electrode 5 increases in the center line C direction of the sheath 2, thereby the high-frequency treatment instrument can be inserted into the channel of the endoscope. On the other hand, in the state where the knife portions 3 are rotated to be substantially perpendicular to the center line C of the sheath 2, it is possible to sufficiently secure the contact area which contacts the pathological lesion portion X.

Next, a second embodiment of the invention will be described with reference to FIGS. 8 to 11.

The same elements as the first embodiment are denoted by the same reference numerals and description thereof will be omitted.

Figure 8:
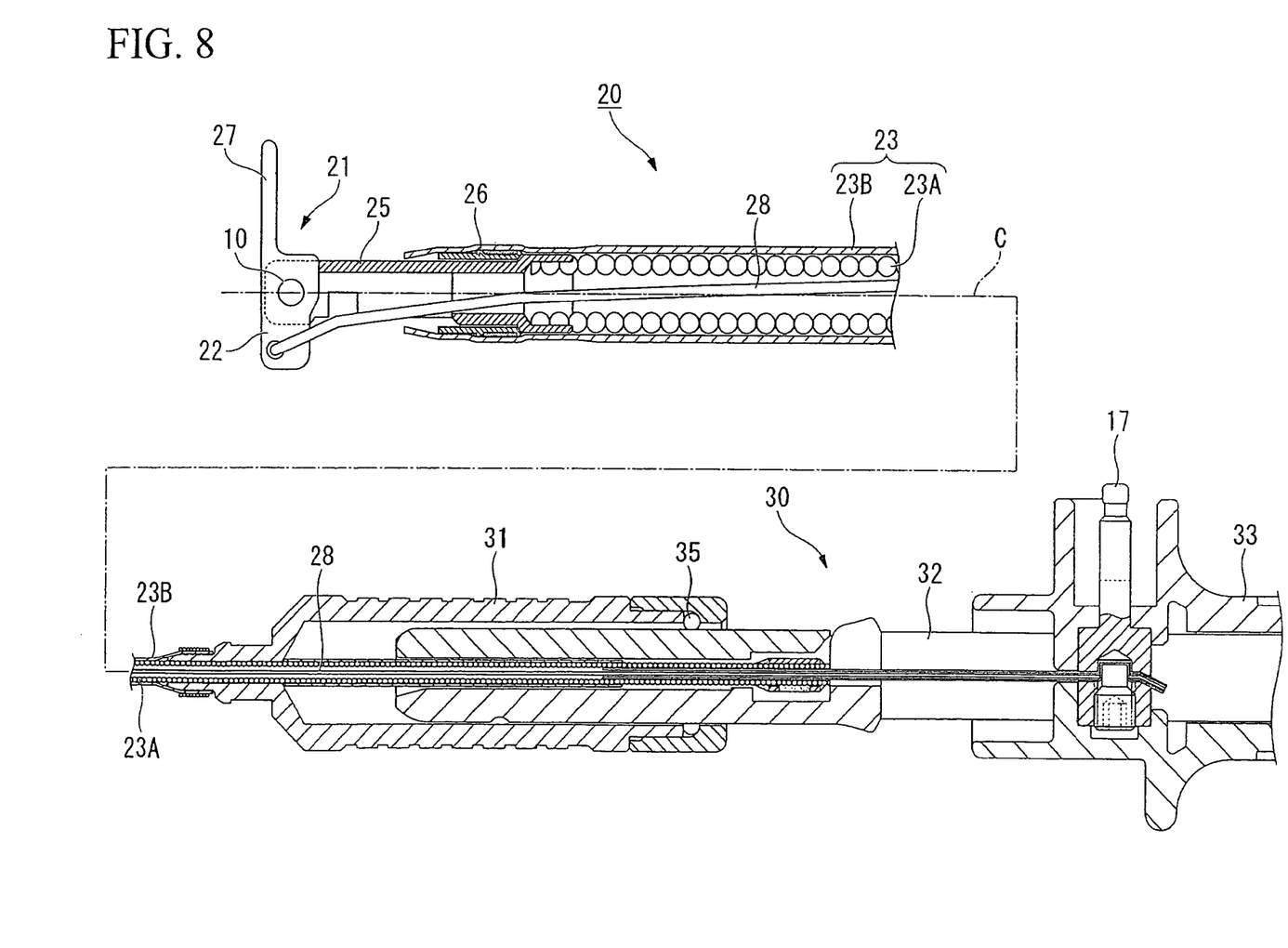
FIG. 8 is a partially sectional schematic view illustrating a whole high-frequency treatment instrument according to a second embodiment of the invention.
Figure 9:
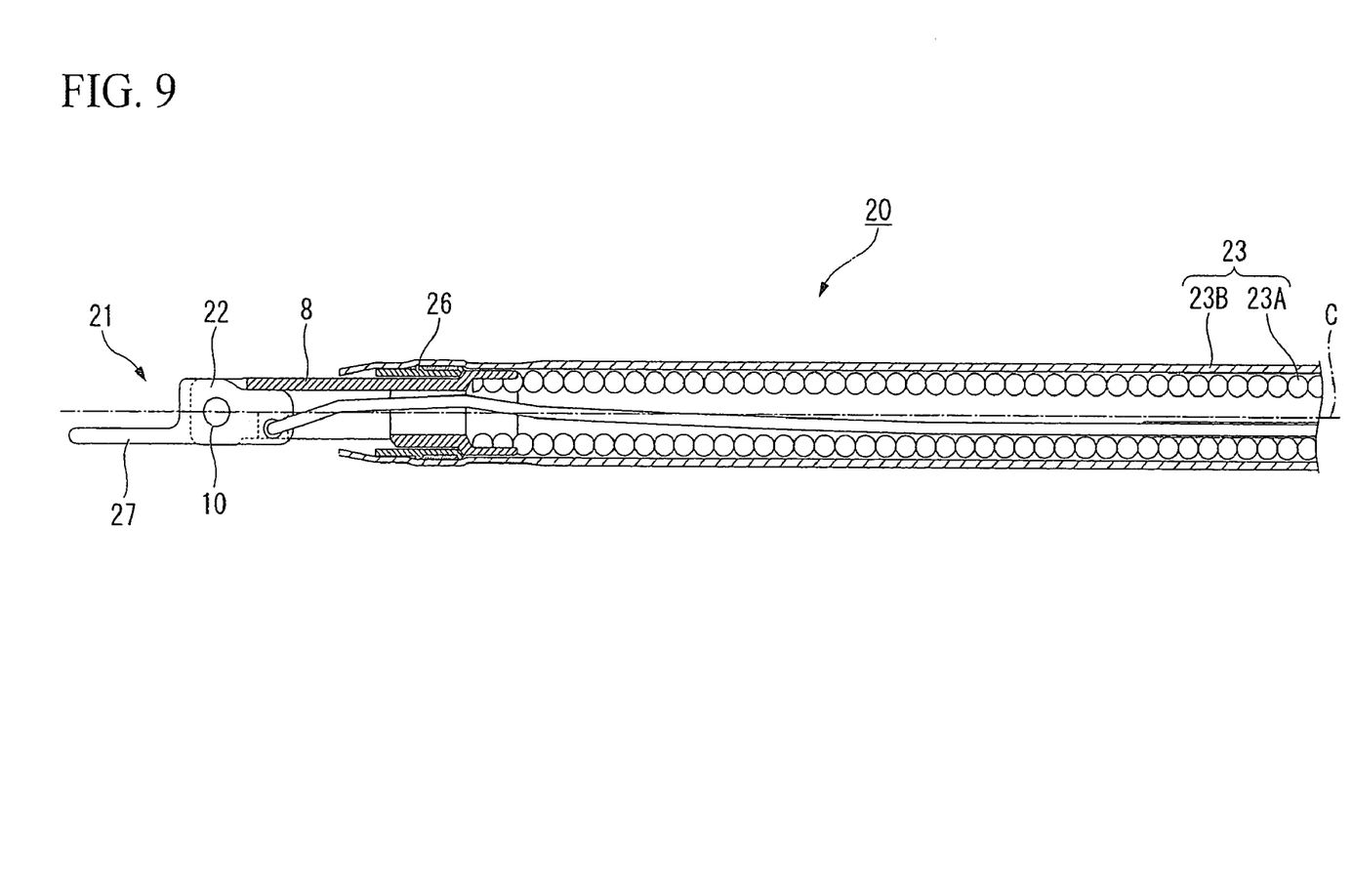
FIG. 9 is a partially sectional plan view of substantial part illustrating the high-frequency treatment instrument according to the second embodiment of the invention.
Figure 10:
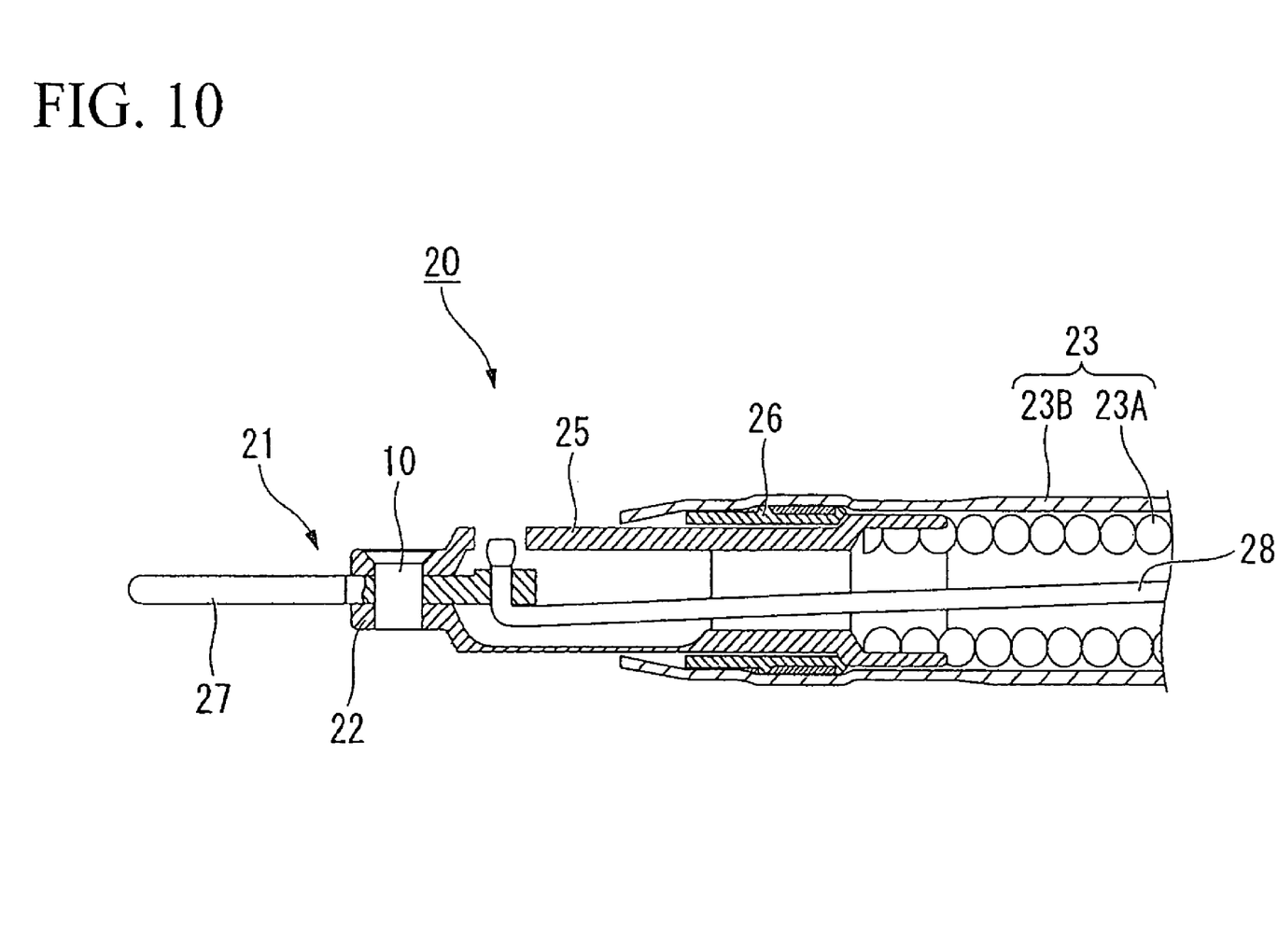
FIG. 10 is a partially sectional side view of substantial part illustrating the high-frequency treatment instrument according to the second embodiment of the invention.

The second embodiment is different from the first embodiment, in that a treatment electrode 21 of a high-frequency treatment instrument 20 according to the second embodiment has only one electrode piece 22, as shown in FIGS. 8 to 10.

A sheath 23 has a coil sheath 23A and a resin tube 23B disposed therein so as to freely advance and retreat with each other. A distal end support portion 25 is connected to a distal end of the coil sheath 23A. The distal end of the resin tube 23B is provided with a locking portion 26 which restricts the protrusion of the coil sheath 23A from the distal end of the resin tube 23B.

The electrode piece 22 has the same shape as the electrode piece 11A according to the first embodiment. A knife portion 27 is formed by allowing a part of a linear portion of the electrode piece 22 to further protrude linearly in the same direction. An operating wire 28 is connected to the electrode piece 22 in a line extending from the proximal end side of the knife portion 27.

An operating portion 30 includes a tube-shaped first slider 31 of which the distal end is connected to the proximal end of the resin tube 23B, a rod-shaped operating portion body 32 to which the proximal end of the coil sheath 23A is connected, and a second slider 33 to which the proximal end of the operating wire 28 is connected. The first slider 31 slidably covers to the outer peripheral surface of the operating portion body 32 with an O ring 35 interposed therebetween. The second slider 33 is slidably connected to the first slider 31 and the operating portion body 32. The electrode terminal 17 is disposed in the second slider 33. A finger laying portion 18 is disposed at the proximal end of the operating portion body 15.

Next, operations of the high-frequency treatment instrument 20 according to this embodiment will be described.

First, similarly to the first embodiment, a physiologic saline solution is locally injected into a submucosal layer around a pathological lesion portion to be removed, thereby distending the pathological lesion portion.

Then, the second slider 33 is made to retreat relative to the operating portion body 32 of the high-frequency treatment instrument 20.

Figure 11:
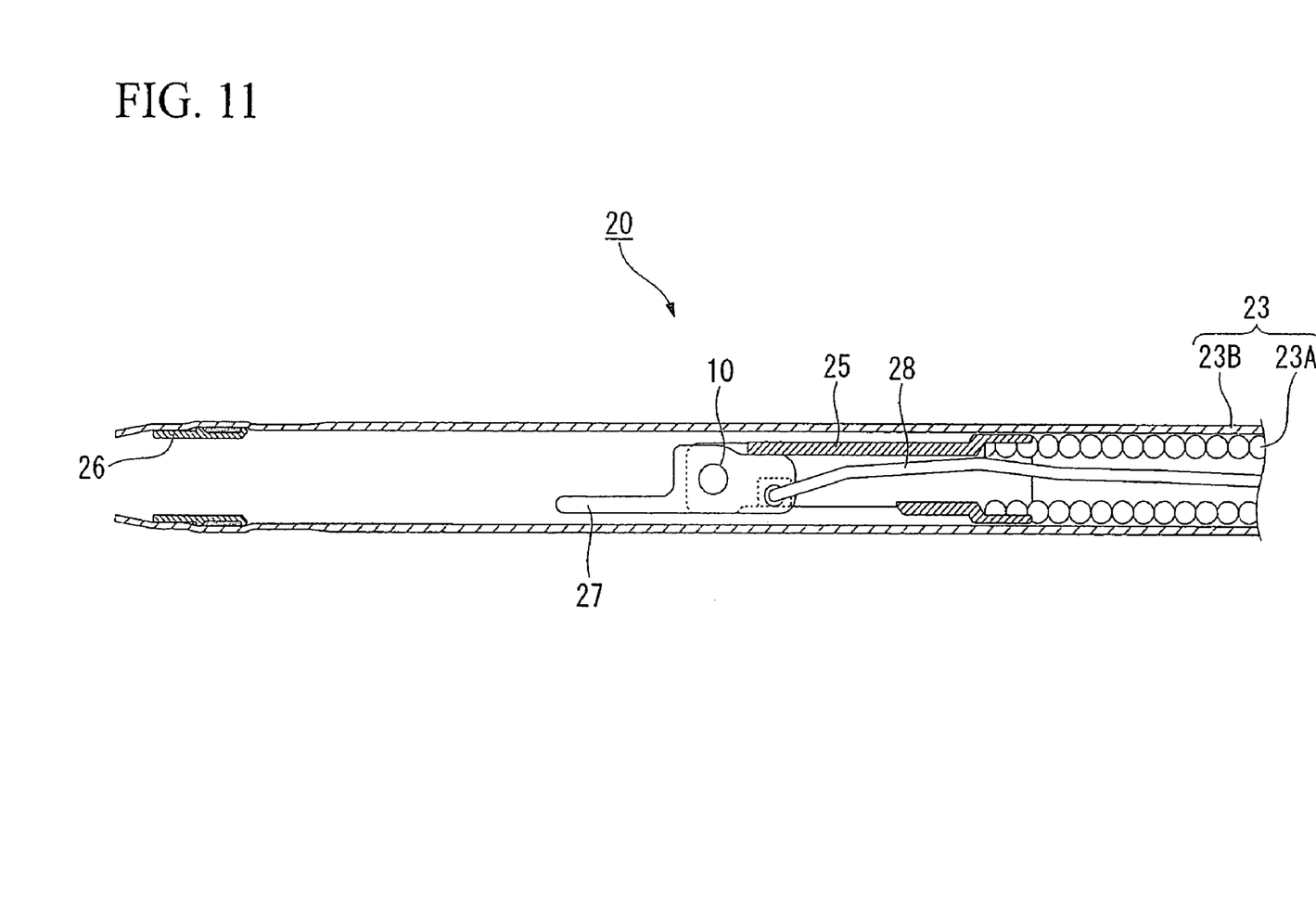
FIG. 11 is a partially sectional plan view of substantial part illustrating the high-frequency treatment instrument according to the second embodiment of the invention.

At this time, the electrode piece 22 rotates around the axis of rotation 10 in a counterclockwise direction in the drawing, whereby the knife portion 27 is substantially parallel to the center line C of the sheath 23. In this state, when the operating portion body 32 is made to retreat relative to the first slider 31, the treatment electrode 21 is further housed in the resin tube 23B, as shown in FIG. 11.

In this state, the sheath 23 is inserted into a treatment instrument channel of an endoscope not shown. Then, the distal end side of the resin tube 23B is exposed from the channel in the vicinity of the pathological lesion portion and the operating portion body 32 along with the second slider 33 is made to move to the distal end side of the operating portion body 32 relative to the first slider 31 until the coil sheath 23A comes in contact with the locking portion 26. At this time, as shown in FIG. 9, the treatment electrode 21 protrudes from the distal end of the sheath 23.

After the coil sheath 23A comes in contact with the locking portion 26, the distal end of the knife portion 27 is brought into contact with a part of the mucous membrane in the vicinity of the pathological lesion portion and then high-frequency current is supplied thereto, thereby forming a hole which is a start point of the entire peripheral cut-out. Then, by individually operating the endoscope and the high-frequency treatment instrument 20, the submucosal layer is exposed while the mucous membrane around the pathological lesion portion is cut out.

Subsequently, the second slider 33 is made to move to the distal end side of the operating portion body 32. At this time, since the operating wire 28 advances relative to the coil sheath 23A, the operating wire 28 presses the electrode piece 22. Then, the electrode piece 22 rotates around the axis of rotation 10 in the clockwise direction in the drawing and the knife portion 27 is extended in a direction substantially perpendicular to the center line C of the sheath 23, as shown in FIG. 8.

The high-frequency current is made to flow thereto while the knife portion 27 is brought into contact with the submucosal layer and the sheath 23 of the high-frequency treatment instrument 20 is made to advance relative to the channel while observing with the endoscope. When the cut-out angle is to be changed, the operating portion body 32 is made to rotate relative to the first slider 31. In this way, the submucosal layer is cut out to dissect the pathological lesion portion, similarly to the first embodiment.

According to the high-frequency treatment instrument 20, when the knife portion 27 becomes substantially parallel to the center line C of the sheath 23, the knife portion 27 can pass in and out of the sheath 23. Accordingly, similarly to the existing high-frequency knife, it is possible to form a hole around the pathological lesion portion. On the other hand, when the knife portion 27 becomes substantially perpendicular to the center line C, the same advantages as the first embodiment can be obtained.

Since the treatment electrode 21 has only one electrode piece 22, it is possible to simplify the distal side configuration of the treatment instrument.

Figure 12:
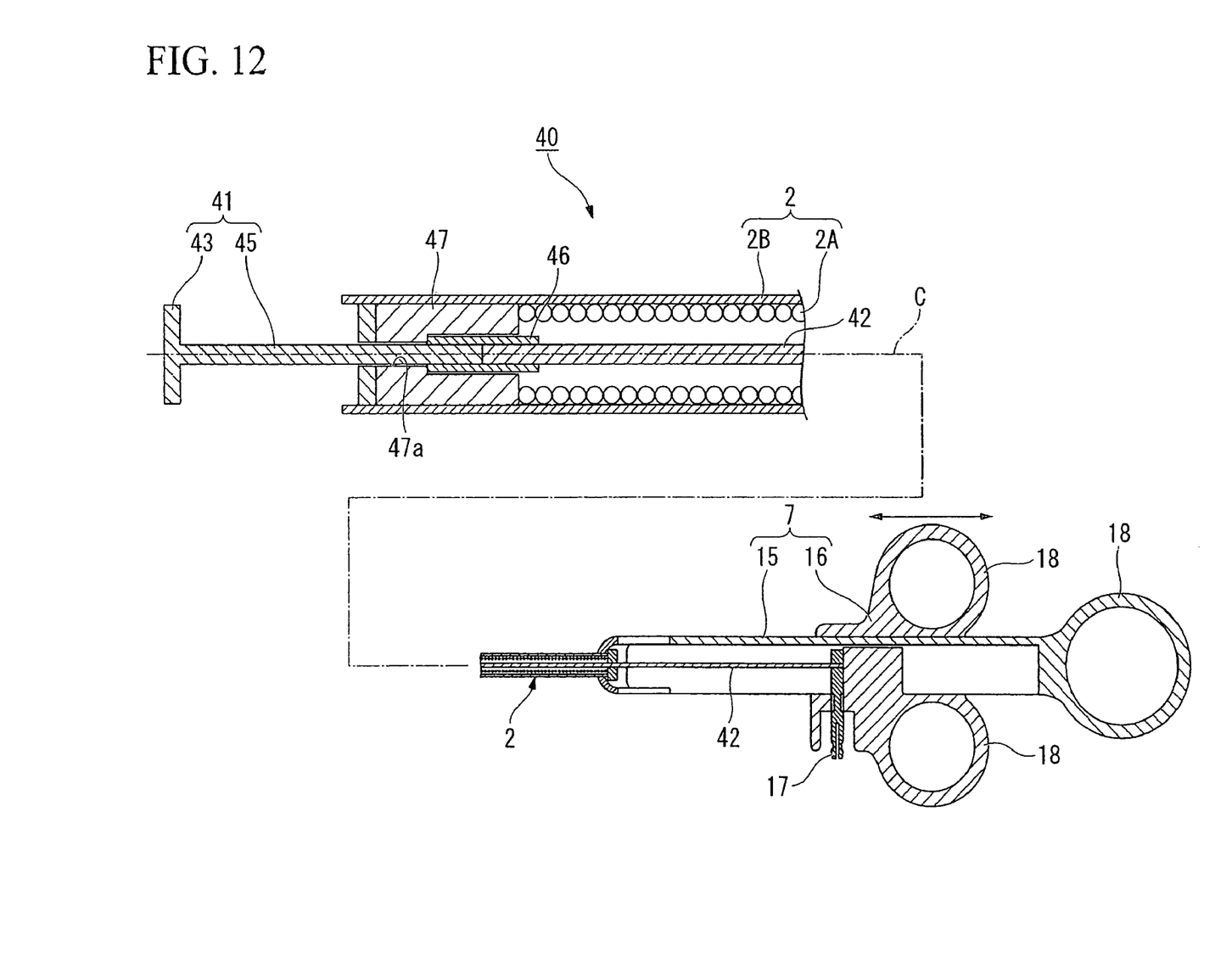
FIG. 12 is a partially sectional schematic view illustrating a whole high-frequency treatment instrument according to a third embodiment of the invention.

Next, a third embodiment of the invention will be described with reference to FIG. 12.

The same elements as the above-mentioned embodiments are denoted by the same reference numerals and description thereof will be omitted.

The third embodiment is different from the first embodiment, in that a treatment electrode 41 of a high-frequency treatment instrument 40 according to the third embodiment is disposed at a distal end of an operating wire 42 so as to advance and retreat in the sheath 2 along with the operating wire 42 and a knife portion 43 is disposed to extend in a direction substantially perpendicular to a center line C of the operating wire 42.

The treatment electrode 41 includes the knife portion 43 and a rod-shaped relay portion 45 which is connected to the operating wire 42. The center of the knife portion 43 is connected to the distal end of the relay portion 45. The knife portion 43 has a length substantially equal to the inner diameter of the sheath 2. The operating wire 42 and the relay portion 45 are connected to each other via a connection member 46.

A control portion 47, which is provided with a through-hole 47a having such a size to allow the relay portion 45 to pass therethrough and not to allow the knife portion 43 and the connection member 46 to pass therethrough, is disposed at the distal end of the sheath 2. That is, the operating wire 42 and the treatment electrode 41 freely rotate relative to the sheath 2.

Next, operations of the high-frequency treatment instrument 40 according to this embodiment will be described.

First, similarly to the first embodiment, a physiologic saline solution is locally inserted into a submucosal layer around a pathological lesion portion to be removed, thereby distending the pathological lesion portion. Then, an injection needle not shown is pulled out of a treatment instrument channel not shown.

Subsequently, the existing high-frequency knife is inserted into the treatment instrument channel and high-frequency current is supplied thereto, thereby forming a hole which is a start point of the entire peripheral cut-out. Then, the submucosal layer is exposed while cutting out the mucous membrane around the pathological lesion portion.

And by pulling the high-frequency knife out of the channel and allowing the slider 16 to retreat relative to the operating portion body 15, in a state where the knife portion 43 is housed in the sheath 2, the sheath 2 of the high-frequency treatment instrument 40 is inserted into the treatment instrument channel.

The distal end of the sheath 2 is exposed from the channel and then the slider 16 is made to move to the distal end side of the operating portion body 15. At this time, until the connection member 46 is locked to the control member 47, the operating wire 42 is made to advance relative to the sheath 2, and thus the treatment electrode 41 protrudes from the sheath 2. Then, high-frequency current is made to flow therein while the knife portion 43 comes in contact with the submucosal layer, and the sheath 2 of the high-frequency treatment instrument 40 is made to advance relative to the channel while observing with the endoscope.

When the cut-out angle is to be changed, the operating portion 7 is made to rotate relative to the endoscope. At this time, a rotation torque is transmitted to the treatment electrode 41 via the operating wire 42 and thus the treatment electrode rotates around the center line C, thereby changes the direction of the knife portion 43. In this way, the submucosal layer is cut out by the knife portion 43 and thus the pathological lesion portion is dissected.

According to the high-frequency treatment instrument 40, since the knife portion 43 of the treatment electrode 41 is extended in the direction substantially perpendicular to the operating wire 42, it is possible to enhance the contact area between the treatment electrode 41 and the pathological lesion portion. In addition, by operating the operating wire 42 so as to advance and retreat, it is possible to bring the treatment electrode 41 into contact with the pathological lesion portion with an appropriate contact area.

In addition, because the operating wire 42 and the treatment electrode 41 are disposed to freely advance and retreat and to freely rotate relative to the sheath 2, when an approach angle of the knife portion 43 relative to the pathological lesion portion is to be changed, rotating only the operating wire 42 without rotating the whole sheath 2 is required, thereby reduces required rotation torque and facilitates the rotation.

The technical scope of the invention is not limited to the above-mentioned embodiments, but various modifications may be made therein without departing from the gist of the invention.

Figure 13:
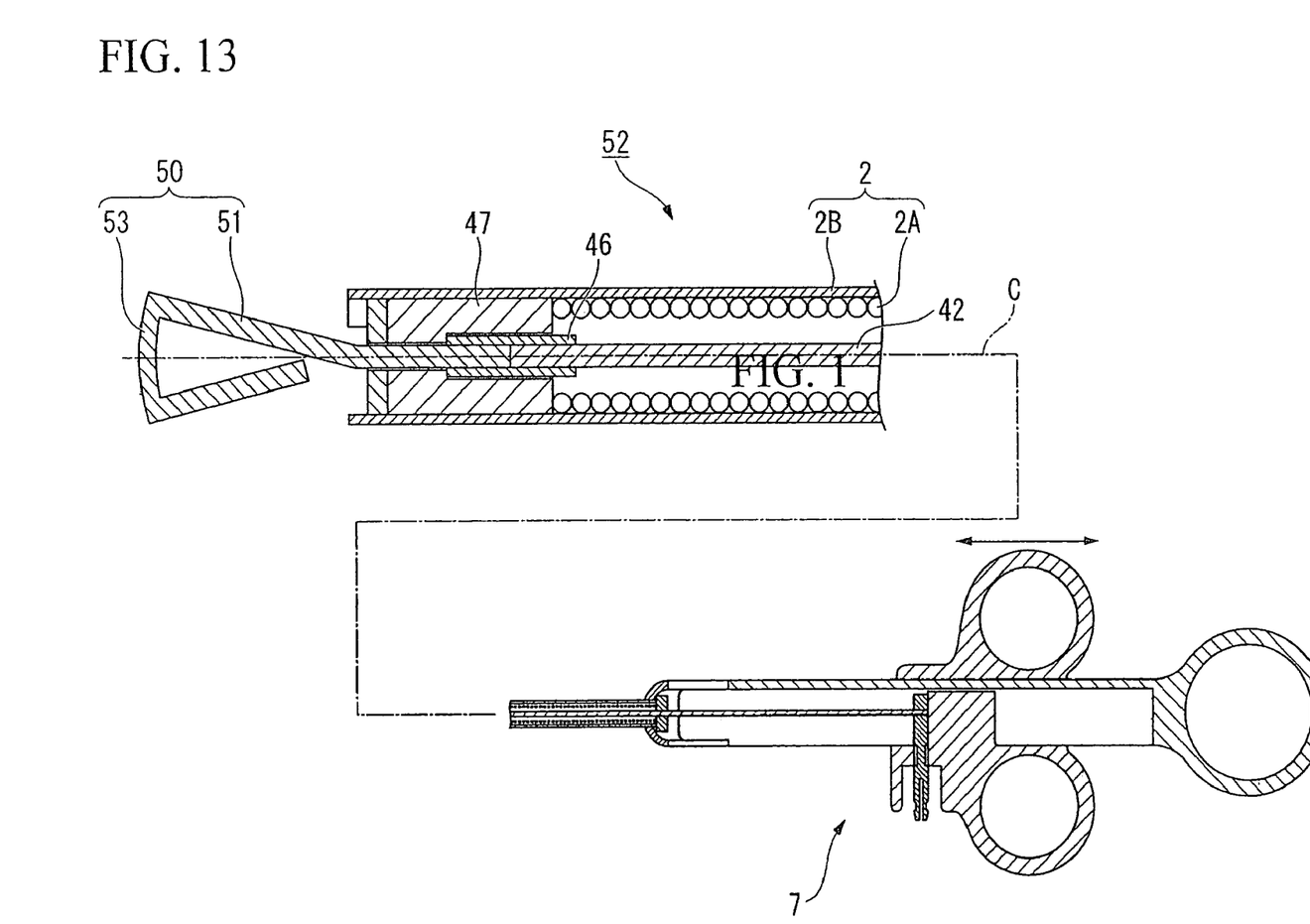
FIG. 13 is a partially sectional schematic view illustrating a whole modified example of the high-frequency treatment instrument according to the third embodiment of the invention.

For example, in the third embodiment, as shown in FIG. 13, a high-frequency treatment instrument 52 may be configured such that a relay portion 51 of a treatment electrode 50 is inclined relative to the center line C of the operating wire 42.

Figure 14:
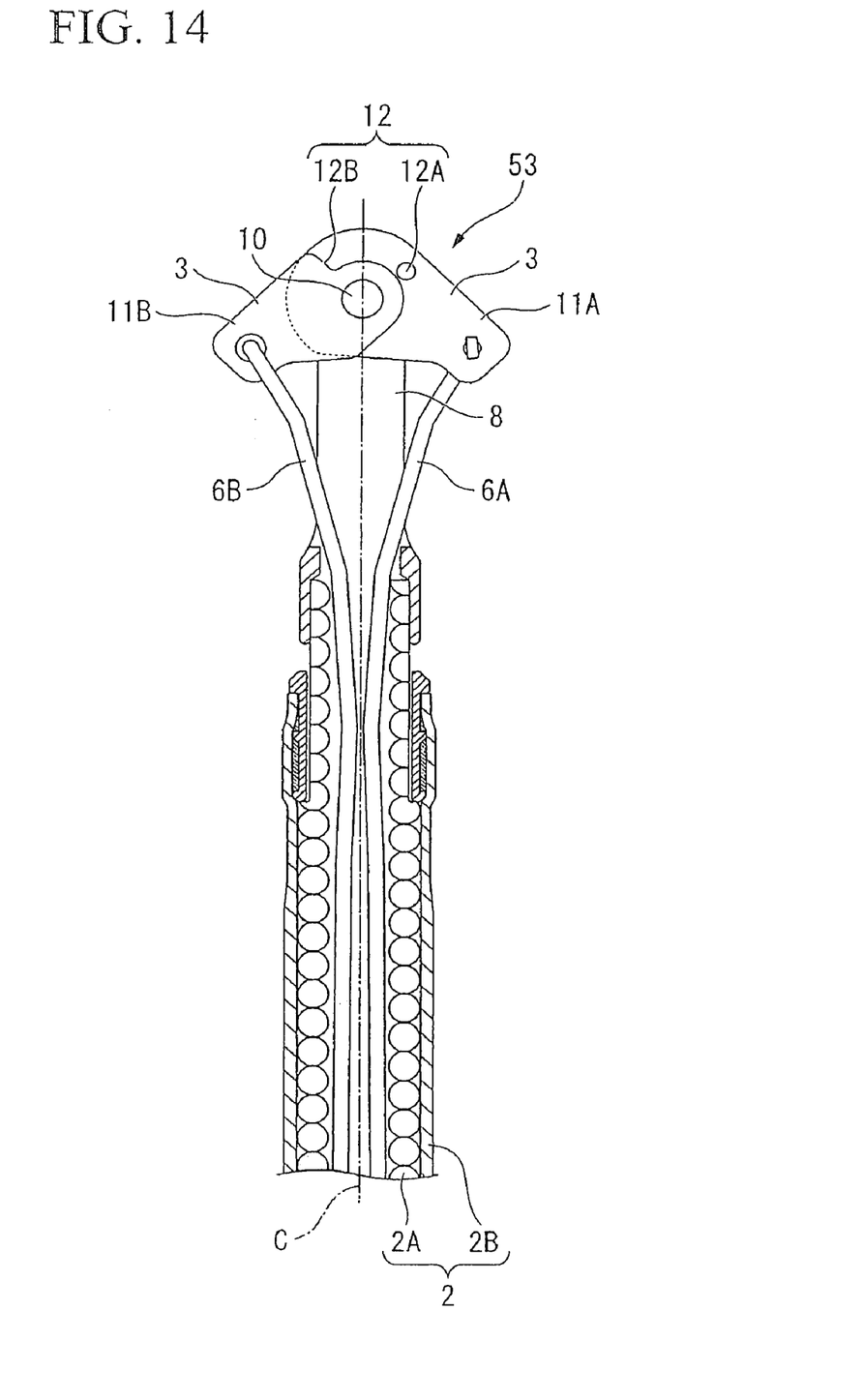
FIG. 14 is a partially sectional plan view of substantial part illustrating the high-frequency treatment instrument according to the first embodiment of the invention.

In the first embodiment, as shown in FIG. 14, by stopping the operation at any position in the way of opening or closing of the pair of electrode pieces 11A and 11B, it is possible to form a mountain-shaped cut-out surface 53 in which the proximal side angle formed by the knife portions 3 is less than 180 degrees. That is, it is possible to adjust the width of the cut-out surface.

Figure 15:
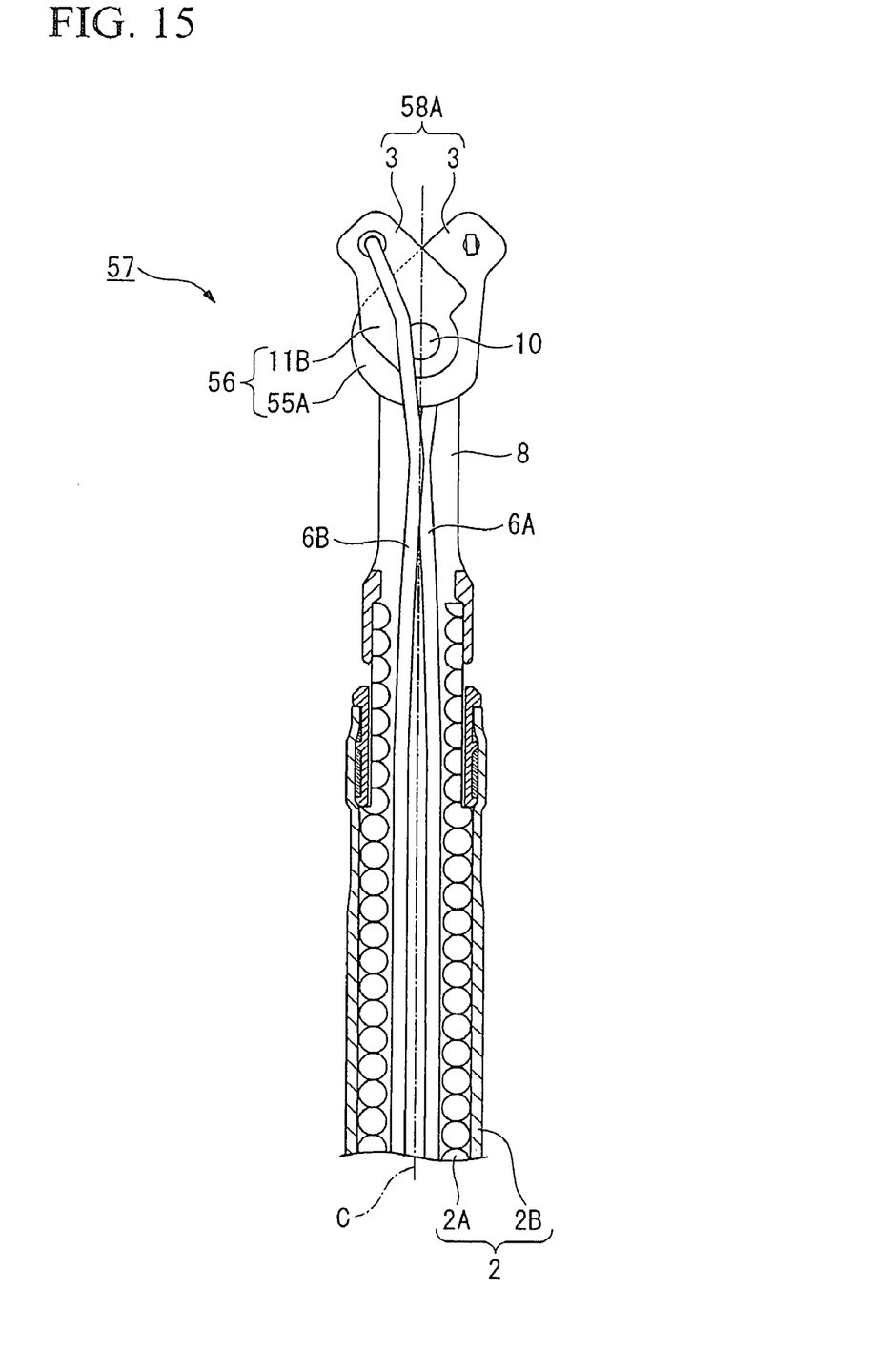
FIG. 15 is a partially-sectional plan view of substantial part illustrating a modified example of the high-frequency treatment instrument according to the first embodiment of the invention.

Further in the first embodiment, instead of the electrode piece 11A of the treatment electrode 5, as shown in FIG. 15, a high-frequency treatment instrument 57 including a treatment electrode 56 having an electrode piece 55A without the convex portion 12A may be used. In this case, by further moving the slider 16 to the distal end side relative to the operating portion body 15, a valley-shaped cut-out surface 58A may be formed in which the proximal side angle formed by the knife portions 3 is greater than 180 degrees. Accordingly, it is possible to stabilize the cutting direction of the knife portions 3 in a state where a pathological lesion portion is placed in the valley-shaped portion of the knife portions 3.

According to the first aspect of the invention, it is possible to bring the knife portion into contact with the subject tissue with an appropriate contact area by adjusting an angle of the knife portion relative to the elongated extension member.

According to the second aspect of the invention, the knife portions can be arranged linearly by allowing the pair of electrode pieces to rotate around a rotation center, thereby securing a large cut-out surface using the knife portions.

According to the third aspect of the invention, it is possible to allow the treatment electrode to rotate and to change the direction of the knife portion by allowing the axial member to advance and retreat relative to the elongated extension member.

According to the fourth aspect of the invention, in the state where the knife portion is substantially parallel to the center line of the elongated extension member, even when the knife portion is elongated, the length of the treatment electrode increases in the center line direction of the elongated extension member, thereby it is possible to insert the knife portion into a treatment instrument channel of an endoscope. On the other hand, in the state where the knife portion is rotated to be substantially perpendicular to the center line of the elongated extension member, it is possible to sufficiently secure the contact area which contacts the subject tissue.

According to the fifth aspect of the invention, since the knife portion has a length longer than the outer diameter of the elongated extension member, it is possible to sufficiently secure the contact area which contacts the subject tissue. In addition, by arranging the knife portion to be substantially parallel to the center line of the elongated extension member, it is possible to house the knife portion in the elongated extension member.

According to the sixth aspect of the invention, since the knife portion of the treatment electrode extends in a direction substantially perpendicular to the axial member, it is possible to increase the contact area between the treatment electrode and the subject tissue. By allowing the axial member to advance and retreat, it is possible to bring the knife portion into contact with the subject tissue with an appropriate contact area.

According to the invention, it is possible to facilitate a procedure by enabling a treatment on a subject tissue without performing a curving operation of an endoscope.

While preferred embodiments of the invention have been described and illustrated above, it should be understood that these are exemplary of the invention and are not to be considered as limiting. Additions, omissions, substitutions, and other modifications can be made without departing from the spirit or scope of the present invention. Accordingly, the invention is not to be considered as being limited by the foregoing description, and is only limited by the scope of the appended claims.

What is claimed is:

1. A high-frequency treatment instrument for performing a high-frequency treatment on a subject tissue, the high-frequency treatment instrument comprising:
   an elongated extension member; and
   a treatment electrode which is rotatably connected to a distal end of the elongated extension member and which has a knife portion extending substantially parallel to a diameter direction of said rotation, wherein
   the treatment electrode has a pair of electrode pieces which rotate reversely to each other around a same rotation center,
   each of the pair of electrode pieces has the knife portion, and
   when the knife portion is substantially perpendicular to an axis of the elongated extension member, a cut-out surface of the knife portion appears at a distal end of the high-frequency treatment instrument.

2. The high-frequency treatment instrument according to claim 1, wherein
   the elongated extension member is formed in a tube shape, and wherein
   the high-frequency treatment instrument further comprises an axial member which is rotatably connected to the treatment electrode and which advances and retreats relative to the elongated extension member to rotate the treatment electrode.

3. The high-frequency treatment instrument according to claim 2, wherein
   the knife portion rotates from a state where the knife portion is substantially parallel to a center line direction of the elongated extension member to a state where the knife portion is substantially perpendicular to the center line direction.

4. The high-frequency treatment instrument according to claim 2, wherein
   the knife portion has a length longer than the outer diameter of the elongated extension member.

5. A high-frequency treatment instrument for performing a high-frequency treatment on a subject tissue, the high-frequency treatment instrument comprising:
   a sheath;
   an axial member disposed in the sheath so as to freely advance and retreat and to freely rotate; and
   a treatment electrode which is disposed at a distal end of the axial member so as to advance and retreat in the sheath along with the axial member and which has a knife portion extending in a direction substantially perpendicular to a center line of the axial member as the axial member being a center, wherein
   the knife portion is rotatable from a direction substantially perpendicular to the center line of the sheath to a direction substantially parallel to the center line of the sheath, and
   when the knife portion rotates from the direction substantially perpendicular to the center line of the sheath to the direction substantially parallel to the center line of the sheath, the knife portion always appears at a distalmost location of the high-frequency treatment instrument.

* * * * *